United States Patent [19]

Stults et al.

[11] Patent Number: 5,089,631
[45] Date of Patent: Feb. 18, 1992

[54] DIOXYDIPHTHALIC ANHYDRIDE

[75] Inventors: Jeffrey S. Stults; Willis T. Schwartz, both of Grand Island, N.Y.

[73] Assignee: Occidental Chemical Corporation, Niagara Falls, N.Y.

[21] Appl. No.: 621,412

[22] Filed: Dec. 3, 1990

Related U.S. Application Data

[62] Division of Ser. No. 492,196, Mar. 13, 1990, Pat. No. 5,003,086, which is a division of Ser. No. 352,070, May 15, 1989, Pat. No. 4,943,642.

[51] Int. Cl.$^5$ .......................................... C07D 493/14
[52] U.S. Cl. .................................... 549/234
[58] Field of Search ......................... 549/234

[56] References Cited

PUBLICATIONS

Erglis et al, Chemical Abstracts, vol. 80 (1974), 48,007m.
Pebalk et al, Chemical Abstracts, vol. 88 (1978) 135,960a.

Primary Examiner—Richard L. Raymond
Attorney, Agent, or Firm—James F. Tao; Arthur S. Cookfair

[57] ABSTRACT

Dioxydiphthalic anhydride is prepared by the reaction of dihalophthalic anhydride with an alkali metal compound, such as potassium carbonate. The compound is particularly useful as a monomer in the preparation of polyimides.

2 Claims, No Drawings

DIOXYDIPHTHALIC ANHYDRIDE

This is a division of application Ser. No. 07/492,196, filed Mar. 13, 1990, now U.S. Pat. No. 5,003,085, which is a division of application Ser. No. 07/352,070, filed May 15, 1989, now U.S. Pat. No. 4,943,642.

BACKGROUND OF THE INVENTION

This invention relates to novel dianhydride compounds. The products are useful chemical intermediates for the further preparation of various compounds such as the corresponding tetracarboxylic acids and the various derivatives thereof, including for example, the salts, esters, acyl halides, amides, imides, and the like. The dianhydrides are particularly useful as curing agents for epoxy resins and as monomers in the preparation of polyimides, for example, by polycondensation with a suitable diamine, such as ethylene diamine or phenylene diamine.

Dianhydrides are commonly used in the preparation of polyesters, by polycondensation with dihydric alcohols and in the preparation of polyimides, by polycondensation with a suitable diamine. A variety of dianhydrides are shown in the literature as monomers in the preparation of such polymers. The properties of the polymer will depend in part on the selection of monomers used in its preparation. Thus, the dianhydrides of this invention as well as those already known and disclosed in literature may be used in a selective manner to achieve the various properties desired in a polyimide.

U.S Pat. No. 4,697,023 discloses the preparation of oxydiphthalic anhydrides and suggest their use in the preparation of polyimides. The oxydiphthalic anhydrides are prepared by the reaction of a halophthalic anhydride with water and an alkali metal compound such as KF, CsF, or $K_2CO_3$ in the presence of a polar aprotic solvent.

Kolesnikov, G. S. et al, *Vysokomol. Soyed*, A9, 612-18 (1967); Marvel, C. S. et al, *J. Am. Chem. Soc.*, 80, 1197 (1958); and Latrova, Z. N. et al, *Volokna Sin. Polim.*, 15-24 (1970), disclose the preparation of oxydiphthalic acids and anhydrides by the oxidation of tetramethyldiphenyl ethers.

German Patent No. 2,416,594 (1975) discloses the preparation of oxydiphthalic anhydride by coupling of 3-nitrophthalic anhydride in the presence of metal nitrites such as sodium nitride.

U.S Pat. No. 3,879,428 to Heath et al discloses the preparation of various aromatic bis(ether anhydrides) by reaction of nitrophthalimide with an alkali diphenoxide followed by hydrolysis to yield the diether anhydride.

Tilika et al, Synthesis of Carboxylic Acids of Aromatic Sulfides, Latv. PSR Zinat. Akad. Vestis, Kim. Ser. (2), 201-4, 1982; CA 97(7):55412U, disclose the reaction of 5-bromo-4-mercaptophthalic acid with $Cu_2O$ to give 80 percent thianthrene-2,3,7,8-tetracarboxylic acid, that is

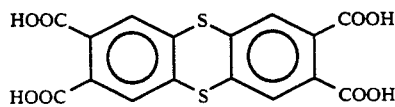

Pebalk et al, Spin Density Distribution In An Anion Radicals of Aromatic Tetracarboxylic Acid Dianhydrides, Dokl. Akad. Nauk, SSSR, 244(5), 1169-73, [Phys. Chem.]1979; CA 90(23):186029c, disclose the EPR spectra of various compounds including a compound of the structure

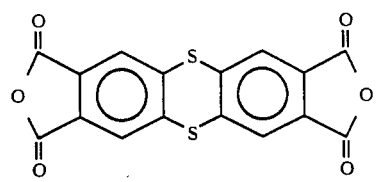

Pebalk et al, Electron-acceptor Properties of Aromatic Dianhydrides, Dokl. Akad. Nauk, SSSR, 236(6), 1379-82 [Chem.]1977, CA 88(19):135960a, disclose the electron-acceptor properties of 15 phthalic anhydrides and condensed phthalic anhydrides including dithiodiphthalic anhydrides.

2,3,7,8-Tetracarboxyphenoxathin dianhydride of the formula

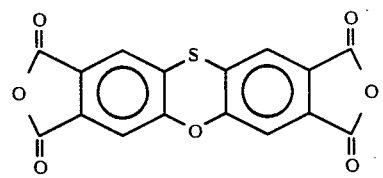

is disclosed by Erglis et al. (USSR Patent No. 395,358; CA 80(9):48007m.) The compound was prepared by the reaction of $(3,4\text{-}Me_2C_6H_3)_2O$ with sulfur in the presence of aluminum chloride followed by oxidation with $KMnO_4$ in aqueous piperidine to form the tetracarboxylic acid, which was cyclized.

SUMMARY OF THE INVENTION

The present invention relates to new aromatic dianhydrides of the formula

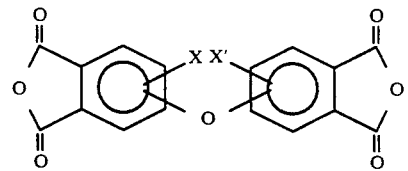

where X is F, Cl, Br or I, X' is H, F, Cl, Br or I, or X and X' may together represent an oxygen atom forming a second ether linkage, with the proviso that when X and X' are taken together to represent an oxygen atom, the ether linkage is positioned at ring carbon sites adjacent to the sites forming the first ether linkage shown. The invention further relates to the acids and acid halides and salts of these anhydrides.

The diphthalic anhydrides of the present invention can be prepared by reacting a dihalophthalic anhydride of the formula

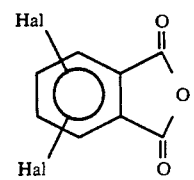

where Hal is F, Cl, Br, or I with water and an alkali metal compound selected from the group consisting of KF, CsF, and K₂CO₃.

In the process, the halogen atoms on the dihalophthalic anhydride reactant function as leaving groups and become the site for the formation of an ether bridge. Thus, when the reactant is a 4,5-dihalophthalic anhydride such as

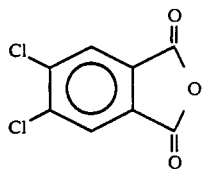
III the reaction products will include 4,4'-oxy-5,5'-dihalophthalic anhydride, characterized on the formula

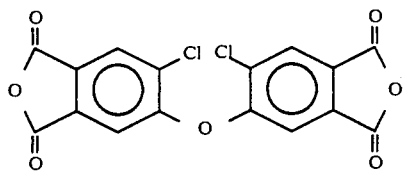
IV and 4,5,4',5'-dioxydiphthalic anhydride characterized by the formula

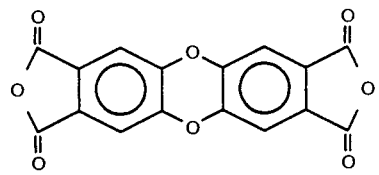
V

The particular halogen atoms at the 5 and 5' positions will depend on the halogen atoms present at the 5 position of the starting dihalophthalic anhydride. Thus, for example, the above oxydichlorodiphthalic anhydride (IV) may be formed from 4,5-dichlorophthalic anhydride starting material. When difluorophthalic anhydride is employed the corresponding oxydifluoro-diphthalic anhydride may be formed. In addition, a monochloro-oxydiphthalic anhydride may be formed by using as a starting reactant a mixture of a monohalophthalic anhydride, such as 4-chlorophthalic anhydride and a dihalophthalic anhydride, such as 4,5-dichlorophthalic anhydride. Furthermore, the ring site of the oxygen bridge(s) as well as the ring site dianhydride produced, may be varied by selective choice of the halophthalic anhydride reactant employed. While not being bound by any particular theory, it is believed that the oxy-dihalo-diphthalic anhydride is formed as an intermediate during the initial stages of reaction. The percentage yield thereof may be enhanced by limiting the time of reaction. Alternatively, by increasing the reaction time, the dioxydiphthalic anhydride produced essentially as the sole product. The halo-substituted oxydiphthalic anhydride is separable from the dioxydiphthalic anhydride by common physical separation means, such as selective recrystallization etc. The dihalo-oxydiphthalic anhydrides are useful as monomers in the preparation of polyimides. Bromo- and/or chloro-substituted dianhydrides may be employed to enhance the fire retardant properties of polyimides prepared therefrom. Fluoro-substituted dianhydrides, prepared for example from difluoro-phthalic anhydride may be employed to improve electrical properties, such as dielectric strength of polyimides. In addition, the presence of fluorine ring substituents should increase the solubility of the polyimide in common solvents.

When the reactant is 3,4-dihalophthalic anhydride, the oxydiphthalic product formed will be 3,3',4,4,'-dioxydiphthalic anhydride, characterized by the formula

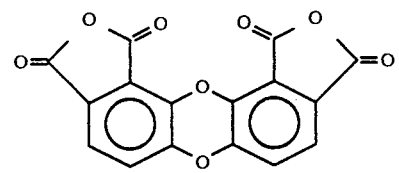
VI

Alternatively, a mixture of the 3,4-dihalo- and 4,5-dihalophthalic anhydrides may be employed as the starting reactant, to form, a dioxydiphthalic anhydride of the formula

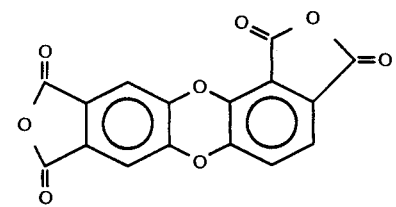
VII

The halogen substituents on the starting halophthalic anhydride reactant may be F, Cl, Br or I. The preferred reactant is 4,5-dichlorophthalic anhydride.

Dioxydiphthalic anhydride, because of its rigid, oxygen-bridged structure, will react with conventional diamines, without flexibilizing bridging units, to form polyimides characterized by a very high glass transition temperature (Tg) and high chemical resistance. Such polyimides would be particularly advantageous for applications where property retention at high temperature and excellent resistance to solvents are required, such as, wire insulation, electrical circuit boards and micro-electronic applications, and as a substrate for vapor deposition.

The alkali metal compound may be potassium fluoride, cesium fluoride, or potassium carbonate, the latter being preferred. The proportions of reactants may vary considerably, however, it is recommended that the alkali metal compound be employed in sufficient proportions to provide at least two equivalents of potassium (or cesium) per mole of dihalophthalic anhydride. Preferably, the alkali metal compound is employed in substantial stoichiometric excess.

Water is a limiting reactant and ideally, for maximum efficiency, is preferably present in a molar proportion of H₂O:dihalophthalic anhydride of about 1.0. The water may be added to the initial reaction mixture or alternatively, may be generated in situ. For example, when potassium carbonate is employed in the reaction mixture, a trace amount of water may be present in the initial reaction mixture and additional water generated in situ as the reaction proceeds.

The process of the invention is preferably carried out at atmospheric pressure, but super-atmospheric pressure, for example under autogenous conditions may be employed, if desired.

The process is preferably carried out neat. However, a solvent may be employed. The preferred solvents are polar, aprotic solvents such as N-methyl pyrrolidone, dimethyl formamide, dimethyl acetamide, triglyme, sulfolane, or the like, the most preferred solvent being sulfolane.

The temperature at which the process is carried out may vary considerably, but will generally be within the range of about 120 to about 230° C. Higher or lower temperatures may be employed, but are less preferred. If a solvent is employed, the choice of the solvent may govern the temperature employed. For example, at atmospheric conditions the boiling point of the solvent may become a limiting condition.

In addition to the dianhydrides prepared in accordance with the process described, this invention is also directed to the acids, acid chlorides, esters and salts derived therefrom. Such derivatives are readily prepared by known reactions. For example, the dianhydride may be converted to the tetracarboxylic acid by hydrolysis and the tetracarboxylic acid may be converted to the corresponding acyl chloride by reaction with a suitable inorganic acid chloride such as thionyl chloride, phosphorus trichloride, or phosphorus pentachloride. The acid chloride may, in turn, be reacted with amines to form amides or diamines to form polyamides. The dianhydride (or tetra-acid) may be reacted with alcohols to form esters or with diols to form polyesters. Furthermore, the dianhydride may be reacted with ammonia to form the corresponding ammonium phthalamate, hydrolyzed to form phthalamic acid, and dehydrated to yield the corresponding di-imide.

The following examples are provided to further illustrate the invention in the manner in which it may be carried out. It will be understood, however, that the specific details given in the examples have been chosen for purposes of illustration only and are not to be construed as limiting the invention. In the examples, unless otherwise indicated, all parts and percentages are by weight and all temperatures are in degrees Celsius.

EXAMPLE 1

Preparation of Dioxydiphthalic Anhydride

A solution of 21.7 grams (0.1 mole) of 4,5-dichlorophthalic anhydride in 40 grams of sulfolane was heated and maintained at 210-215° C. while 0.215 grams of tetraphenylphosphonium bromide was added followed by the incremental addition of 13.82 grams (0.1 mole) of potassium carbonate over a period of about 4 hours. The temperature was maintained an additional hour and the reaction mixture was then cooled to room temperature. Acetone (100 ml) was added and mixed. The reaction mixture was filtered and the solids washed consecutively with another 100 ml of acetone, two 100 ml portions of water, and again with a 100 ml of acetone, to yield about 15 grams of brown solid. After drying, the solid was recrystallized from about 225 grams of 1,2,4-trichlorobenzene to yield 12.5 grams of a tan colored crystalline solid. Mass spectral analysis indicated the product to have a molecular weight of 324 with a fragmentation consistent with dioxydiphthalic anhydride. The identification of dioxydiphthalic anhydride was confirmed by infra-red analysis and $C^{13}$ NMR (CP/MAS).

EXAMPLE 2

Preparation of Dioxydiphthalic Anhydride 4,5-Difluorophthalic anhydride (18.4 grams, 0.1 mole) was dissolved in 40 grams of anhydrous sulfolane and heated to 165° C. with stirring. Tetraphenylphosphonium bromide (0.184 grams, 0.0004 mole) and 1.8 grams (0.10 mole) of water were added and the temperature increased to 200° C. Anhydrous potassium fluoride (23.3 grams, 0.4 mole) was added with stirring. The reaction mixture was held at about 200° C. with stirring for about 3½ hours at which time another 0.2 grams of water was added and the reaction mixture was maintained at temperature for an additional hour. The reaction mixture was cooled to less than 150° C. and 35 grams of acetone added and the solids filtered off. The solids were washed with acetone followed by three 100 ml washes with distilled water. The solid material was dried at 150° C. for 16 hours to yield 15.5 grams (95.7% yield) of dioxydiphthalic anhydride.

EXAMPLE 3

Preparation of Dioxydiphthalic Acid

Dioxydiphthalic anhydride (3.0g, 0.009 mole) was added to 95g of water and heated to reflux. The dianhydride was dissolved by the addition of 4 ml of 40% NaOH. The resulting brown solution was decolorized with 0.2g of activated carbon at reflux for 0.5 hour followed by filtration through celite. Acidifying with 12N HCl to a pH of less than 1 followed by a water wash and drying gave 1.9g of product as confirmed by FTIR. DSC melting point was 260° C. with loss of water.

EXAMPLE 4

This example illustrates the manner in which chlorooxydiphthalic anhydride may be prepared.

A solution of equal molar amounts of 4-chlorophthalic anhydride (18.2 g, 0.1 mole) and 4,5-dichlorophthalic anhydride (21.7 g, 0.1 mole) in 60 g of sulfolane is heated to 180-210° C. Temperature is maintained, with stirring, while 0.05 mole (6.91 g) of potassium carbonate is added over a period of about one hour. The temperature is maintained for an additional two hours, then lowered to room temperature.

EXAMPLE 5

Potassium fluoride (5.04 g) and Carbowax MPEG 2000 (0.71 g) were added to and mixed with 10.2 g of a mixture of 56.1% (GC area percent) 4,5-difluorophthalic anhydride and 43.9% (GC area percent) 4-chloro-5-fluorophthalic anhydride. The powdery mixture was heated in a flask to 180° C., forming a viscous, paste-like reaction mixture. The temperature was maintained at 180-207° C. for approximately 3.5 hours, during which a portion of the reaction mixture sublimed and condensed on the upper portion of the flask. The flask was cooled to room temperature and the sublimate collected (6.69 g) and analyzed by gas chromatography, indicating, in area percent, 74% 4,5-difluorophthalic anhydride and 26% 4-chloro-5-fluorophthalic anhydride. The reaction mixture remaining at the bottom of the flask (7.58 g) was analyzed by gas chromatography and found to contain in area percent, 50.1% 4,5-difluorophthalic anhydride; 42.8% 4-chloro-5fluorophthalic anhydride; 3.4% 4,4'-difluoro-5,5'-oxydiphthalic anhydride; 2.1% 4-chloro-4'-fluoro-5,5'-oxydiphthalic anhydride; 0.3% 4,4'-dichloro-5,5'-oxydiphthalic anhydride and 1.0% 4,4', 5,5'-dioxydiphthalic anhydride.

EXAMPLE 6

Preparation of Polyimide 4,4'-Oxydianiline (ODA) (0.05g, 0.0025 mole) was dissolved in 7.4 grams of dimethylacetamide. Dioxydiphthalic anhydride (0.81g, 0.0025 mole) was added and the mixture stirred overnight to yield a clear, extremely thick solution of the polyamic acid. The inherent viscosity was found to be 1.89.

The polyamic acid solution was coated on a sodalime glass plate and placed in a chamber with dry nitrogen passing through it to remove most of the dimethylacetamide. The plate was then transferred to an oven with a heating program of 100° C. for one hour followed by one hour each at 200 and 300°) C.

The cured polyimide film had good integrity, creasibility and toughness. No glass transition temperature could be detected by DSC at temperature to 450° C.

EXAMPLE 7

Preparation of Copolyimide 4,4'-Oxydianiline (0.5g, 0.0025 mole) was dissolved in 7.33g of dimethylacetamide. To this solution was added 0.194g (0.000625 mole) of oxydiphthalic anhydride and 0.608g (0.001825 mole) of dioxydiphthalic anhydride. The solution was allowed to react overnight, with stirring, to form a polyamic acid having an inherent viscosity of 1.26.

Following the procedure of Example 6, a film of the polyamic acid was formed and imidized. The curved polyimide film was characterized by good integrity, creasibility and toughness. No glass transition temperature could be detected by DSC at temperatures to 450° C.

EXAMPLES 8-9

Preparation of Co-polyimide

The procedure of Example 7 was repeated except that the molar ratio of dioxydiphthalic anhydride (DODPA): oxydiphthalic anhydride (ODPA) was varied as shown in the Table below. The polyamic acid formed using equimolar amounts of DODPA and ODPA had an inherent viscosity of 0.94 while the polyamic acid formed from a 1:3 molar ration of DODPA:ODPA had an inherent viscosity of 1.29. Each of the cured polimide films was tough and creasible and characterized by the physical properties shown in the table.

EXAMPLE 10C

For purposes of comparison, a polyimide was prepared, following the general procedure of Examples 7-9, but using oxydiphthalic anhydride as the only anhydride component.

TABLE

| Dianhydride Compositon (ratio DODPA:ODPA) | Examples | | | | |
|---|---|---|---|---|---|
| | 6 100% DODPA | 7 3:1 | 8 1:1 | 9 1:3 | 10C 100 ODPA % |
| Tg (°C.) | none detected | none detected | 300 | 270 | 265 |
| TGA - Temperature 10% wt loss (°C.) | 580 | 565 | 580 | 570 | 570 |
| Tensile Strength (psi) (ASTM D882) | 10,500 | 18,800 | 17,800 | 17,100 | 19,400 |
| Tensile Modulus (psi) (ASTM D882) | 530,200 | 469,600 | 514,100 | 376,800 | 497,500 |
| Elongation (%) (ASTM D882) | 8.4 | 13.1 | 9.8 | 14.3 | 13.2 |

What is claimed is:

1. A dioxydiphthalic anhydride characterized by the formula

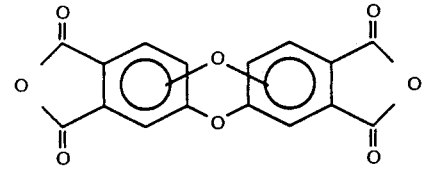

2. 4,5,4', 5'-Dioxydiphthalic anhydride according to claim 1, characterized by the formula

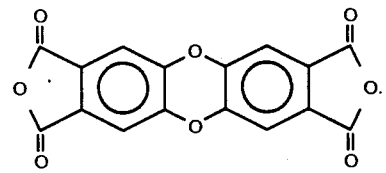

* * * * *